(12) United States Patent
Hosono et al.

(10) Patent No.: US 11,433,378 B2
(45) Date of Patent: Sep. 6, 2022

(54) INTERMETALLIC COMPOUND, HYDROGEN STORAGE/RELEASE MATERIAL, CATALYST AND METHOD FOR PRODUCING AMMONIA

(71) Applicants: JAPAN SCIENCE AND TECHNOLOGY AGENCY, Kawaguchi (JP); TOKYO INSTITUTE OF TECHNOLOGY, Meguro-ku (JP)

(72) Inventors: Hideo Hosono, Meguro-ku (JP); Yutong Gong, Meguro-ku (JP); Jiazhen Wu, Meguro-ku (JP); Masaaki Kitano, Meguro-ku (JP); Toshiharu Yokoyama, Meguro-ku (JP); Yangfan Lu, Meguro-ku (JP); Tiannan Ye, Meguro-ku (JP)

(73) Assignees: JAPAN SCIENCE AND TECHNOLOGY AGENCY, Kawaguchi (JP); TOKYO INSTITUTE OF TECHNOLOGY, Meguro-ku (JP)

( * ) Notice: Subject to any disclaimer, the term of this patent is extended or adjusted under 35 U.S.C. 154(b) by 314 days.

(21) Appl. No.: 16/630,269

(22) PCT Filed: Jul. 12, 2018

(86) PCT No.: PCT/JP2018/026287
§ 371 (c)(1),
(2) Date: Jan. 10, 2020

(87) PCT Pub. No.: WO2019/013272
PCT Pub. Date: Jan. 17, 2019

(65) Prior Publication Data
US 2020/0164348 A1    May 28, 2020

(30) Foreign Application Priority Data
Jul. 12, 2017    (JP) .............................. JP2017-135875

(51) Int. Cl.
*B01J 23/83* (2006.01)
*C01C 1/04* (2006.01)

(52) U.S. Cl.
CPC ............. *B01J 23/83* (2013.01); *C01C 1/0411* (2013.01)

(58) Field of Classification Search
CPC .......... B01J 23/83; C01C 1/0411; C01B 6/00; C01B 3/508
(Continued)

(56) References Cited

U.S. PATENT DOCUMENTS 3,770,658 A * 11/1973 Ozaki ..................... B01J 23/76
502/178
4,142,300 A * 3/1979 Gruen ................... C01B 3/0057
34/416

(Continued)

FOREIGN PATENT DOCUMENTS

| CN | 1236669 A | 12/1999 |
|---|---|---|
| EP | 3 395 441 A1 | 10/2018 |

(Continued)

OTHER PUBLICATIONS

Supporting information for "Tiered Electron Anions in Multiple Voids of LaScSi and Their Applications to Ammonia Synthesis," by Jiazhen Wu et al. (Advanced Materials, vol. 29, No. 38, pp. 5013-5021). (Year: 2017).*

(Continued)

*Primary Examiner* — Patricia L. Hailey
(74) *Attorney, Agent, or Firm* — Oblon, McClelland, Maier & Neustadt, L.L.P.

(57) ABSTRACT

Provided are an intermetallic compound having high stability and high activity, and a catalyst using the same. A hydrogen storage/release material containing an intermetallic compound represented by formula (1): RTX . . . (1)

(Continued)

wherein R represents a lanthanoid element, T represents a transition metal in period 4 or period 5 in the periodic table, and X represents Si, Al or Ge.

9 Claims, 3 Drawing Sheets

(58) Field of Classification Search
USPC .............. 502/303, 355; 423/352, 359, 362; 420/416, 455, 460, 900
See application file for complete search history.

(56) References Cited

U.S. PATENT DOCUMENTS

| | | | | |
|---|---|---|---|---|
| 4,276,060 | A | * | 6/1981 | Aldridge ................ C01B 3/508 376/308 |
| 4,325,931 | A | | 4/1982 | Lewis |
| 4,609,599 | A | * | 9/1986 | Percheron nee Guegan ............... C22C 19/00 429/218.2 |
| 4,863,707 | A | * | 9/1989 | McShea, III ............ C01B 3/382 423/359 |
| 5,738,953 | A | * | 4/1998 | Lichtenberg .......... H01M 4/383 429/59 |
| 5,935,732 | A | * | 8/1999 | Matsumura ........... B22F 1/0088 429/218.2 |
| 6,066,415 | A | * | 5/2000 | Sakai .................... C01B 3/0031 429/218.2 |
| 6,068,948 | A | * | 5/2000 | Imoto ................... H01M 4/383 429/218.2 |
| 10,695,751 | B2 | * | 6/2020 | Hosono ..................... C22C 5/04 |
| 10,759,668 | B2 | * | 9/2020 | Hosono ................. B01J 23/462 |
| 10,792,645 | B2 | * | 10/2020 | Hosono ................. B01J 37/086 |
| 2004/0170520 | A1 | * | 9/2004 | Maeda ................. H01M 4/385 420/441 |
| 2004/0194577 | A1 | * | 10/2004 | Fetcenko ............. H01M 4/383 75/255 |
| 2005/0255382 | A1 | * | 11/2005 | Young .................. C01B 3/0047 429/218.2 |
| 2007/0077491 | A1 | * | 4/2007 | Burchardt ............ H01M 4/242 429/218.2 |
| 2011/0229755 | A1 | * | 9/2011 | Sugii ....................... C22C 19/03 429/163 |
| 2019/0314805 | A1 | * | 10/2019 | Leidinger ................ B01J 23/63 |

FOREIGN PATENT DOCUMENTS

| | | |
|---|---|---|
| JP | 6-340557 A | 12/1994 |
| JP | 7-118171 A | 5/1995 |
| JP | 2006-231229 A | 9/2006 |
| WO | WO 2017/111028 A1 | 6/2017 |

OTHER PUBLICATIONS

R. A. Guidotti et al., "Hydrogen Absorption by Rare Earth-Transition Metal Alloys." Journal of the Less-Common Metals, 52, pp. 13-28. (Year: 1977).*

Sachin Gupta et al., "Review on magnetic and related properties of RTX compounds." Journal of Alloys and Compounds 618, pp. 562-606. (Year: 2015).*

Jiazhen Wu et al., "Intermetallic Electride Catalyst as a Platform for Ammonia Synthesis." Angewandte Chemie International Edition, 58, pp. 825-829. (Year: 2019).*

International Search Report dated Oct. 9, 2018 in PCT/JP2018/026287 filed Jul. 12, 2018, 2 pages.

Takeya et al., "Soybean Oil Hydrogenation Using Hydrogen Storage Alloy (Novel Method of Edible Oil Hydrogenation Part III)," Nippon Shokuhin Kagaku Kogaku Kaishi, vol. 43, No. 5, May 15, 1996, pp. 502-509 (with English abstract).

Imamura et al., "Catalytic transfer hydrogenation of butene on hydrogen-absorbing alloys ($LaNi_5$, $CaNi_5$ and $LaNi_4l$)," Journal of Alloys and Compounds, vol. 323-324, 2001, pp. 601-604.

Jennings et al., "Intermetallic catalysts for methanol synthesis: ternary alloys containing copper and cerium," Applied Catalysis A: General, vol. 81, No. 2, 1992, pp. 257-272.

Snijder et al.. "Hydrogenation of Cyclohexene With $LaNi_{5-x}Al_xH_n$ Metal Hydrides Suspended in Cyclohexane or Ethanol," Chemical Engineering Science, vol. 48, No. 13, 1993, pp. 2429-2441.

Coman et al., "Icosahedral AlMnLn (Ln=Ce, Gd, Dy, Ho) Alloys—An Exafs Study and Catalytic Behavior," Revue Roumaine Chimie, vol. 57, Nos. 4-5, 2012 pp. 521-529.

Takeshita et al., "Rare Earth Intermetallics as Synthetic Ammonia Catalysts," Journal of Catalysis, vol. 44, No. 2, 1976, pp. 236-243.

Wallace, "Rare Earth and Actinide Intermetallics as Hydrogenation Catalysts," Proceedings of an International Symposium Held in Gelio, Norway, Aug. 14-19, 1977, pp. 501-514.

Zhu, "Room temperature catalytic ammonia synthesis over an $AB_5$-type intermetallic hydride," Journal of Alloys and Compounds, vol. 240, 1996, pp. L1-L3.

Extended European Search Report dated Mar. 5, 2021 in European Patent Application No. 18831926.3, 9 pages.

Chevalier, B., et al., "New Hydrides REScSiH and REScGeH (RE=La, Ce): Structure, Magnetism, and Chemical Bonding", Chem. Mater. Sep. 14, 2010, vol. 22, No. 17, XP055779303, pp. 5013-5021.

Wu, J., et al., "Tiered Electron Anions in Multiple Voids of LaScSi and Their Applications to Ammonia Synthesis", Advanced Materials, vol. 29, No. 36, XP055779299, Sep. 1, 2017, 1700924(pp. 1-7).

Gong, Y., et al., "Ternary intermetallic LaCoSi as a catalyst for $N_2$ activation", Nature Catalysis, vol. 1, No. 3, Jan. 22, 2018, XP055779292, pp. 178-185 with cover page.

* cited by examiner

INTERMETALLIC COMPOUND, HYDROGEN STORAGE/RELEASE MATERIAL, CATALYST AND METHOD FOR PRODUCING AMMONIA

TECHNICAL FIELD

The present invention relates to an intermetallic compound, a transition metal-supported intermetallic compound, a hydrogen storage/release material, a catalyst and a method for producing ammonia using the catalyst.

BACKGROUND ART

In the Haber-Bosch process, a typical process for synthesizing ammonia, ammonia is produced by using doubly promoted iron containing $Fe_3O_4$ and a few % by mass of $Al_2O_3$ and $K_2O$ as a catalyst and contacting the catalyst with a mixed gas of nitrogen and hydrogen under a high temperature, high pressure condition.

Meanwhile, studies have been conducted on a process for synthesizing ammonia at a temperature lower than the reaction temperature applied in the Haber-Bosch process, and a study proposes a process using ruthenium (Ru) supported on various carriers as a catalytically active component as a catalyst for ammonia synthesis (for example, Patent Literature 1). It has been known that since catalysts using a transition metal such as Ru have a very high activity, ammonia can be synthesized with them under reaction conditions milder than those in the Haber-Bosch process. For example, although the Haber-Bosch process requires a reaction temperature of 400° C. or more and a reaction pressure of 10 MPa or more, in the case of a catalyst using Ru, reaction progresses at a reaction temperature of about 200° C. and a reaction pressure of 1.1 MPa or less, or even about atmospheric pressure.

Furthermore, intermetallic compounds have been considered as another catalyst for ammonia synthesis. An intermetallic compound of a transition metal such as Ru having high catalytic activity with other metal elements is a promising, inexpensive catalyst.

Examples of intermetallic compounds active in the synthesis of ammonia include intermetallic compounds of an alkali metal or alkaline earth metal and a transition metal, such as $CaNi_5$, $Mg_2Ni$ and $Mg_2Cu$ (Patent Literature 2) and intermetallic compounds such as $CeFe_2$, $CeCo_2$ and $CeRu_2$, which are known as a hydrogen storage alloy (Non Patent Literatures 1, 2). More specifically, Non Patent Literature 1 reports the results of synthesis of ammonia using a powder of an intermetallic compound such as $CeFe_2$, $CeRu_2$ or $CeCo_2$, which has been prepared by a melting method while substituting the catalyst with a metal itself.

Furthermore, a method using the hydride $AB_5H_{-6}$ prepared by reducing an intermetallic compound represented as an $AB_5$-type intermetallic compound as a catalyst has been proposed. More specifically, the study reports that ammonia can be synthesized at room temperature by using, as a catalyst, a hydride prepared by reducing the above $AB_5$-type intermetallic compound wherein A is a misch metal containing La as a main component and B is Ni and which has a BET specific surface area of 0.02 $m^2/g$ (Non Patent Literature 3).

It has also been known that intermetallic compounds are embrittled and crushed due to storage of hydrogen and a fine intermetallic compound is obtained due to release of hydrogen.

CITATION LIST

Patent Literature

Patent Literature 1: JP-A-2006-231229
Patent Literature 2: U.S. Pat. No. 4,325,931

Non Patent Literature

Non Patent Literature 1: Takeshita, T., Wallace, W. E., Craig, R. S., "Journal of Catalysis" 44, 236-243(1976)
Non Patent Literature 2: Wallace, W. E., "Proceedings of an International Symposium Held in Gelio", Norway, 14-19 Aug. 1977 pages 501-514
Non Patent Literature 3: Hai-Yan Zhu, "Journal of Alloys and Compounds" 240(1996) L1-L3

SUMMARY OF THE INVENTION

Technical Problem

However, when intermetallic compounds are used as a catalyst for ammonia synthesis reaction, they are often decomposed into nitride of a rare earth element and a transition metal itself at about a temperature at which the reaction occurs (e.g., about 400° C.), and thus are poor in stability and durability as a catalyst. For example, in Non Patent Literature 1, the results of X-ray diffraction analysis conducted after ammonia synthesis reaction show that the intermetallic compound used as a catalyst was decomposed. Non Patent Literature 1 further reports that the results of the experiment show that transition metals themselves such as Fe, Co and Ru are considered to exhibit catalytic activity. Furthermore, Non Patent Literature 2 describes that $CeCo_3$, $CeRu_2$, $CeFe_2$ and the like are converted into nitride of a rare earth metal and a transition metal itself in the ammonia synthesis reaction, and what actually functions as a catalyst is considered to be a transition metal itself such as Co, Ru or Fe supported on the nitride of a rare earth metal. Moreover, the catalytic activity of intermetallic compounds cannot be said to be high enough.

Thus, an object of the present invention is to provide an intermetallic compound having high stability and activity, and a catalyst using the same.

Solution to Problem

The present inventors have synthesized various intermetallic compounds and have studied their properties, and as a result have found that a ternary intermetallic compound represented by the following formula (1) exhibits ammonia synthesis activity at a temperature and a pressure lower than those in the case of using conventional catalysts, and also have found that the ammonia synthesis activity is greatly improved when a transition metal is supported on the intermetallic compound. The present inventors also have found that the above intermetallic compound characteristically stores/releases hydrogen at a temperature lower than that in the case of using conventional catalysts, which is specifically usually 400° C. or less, and the intermetallic compound which has stored hydrogen can be used for hydrogenation reaction of other compounds.

Accordingly, the present invention provides the following [1] to [16].

[1] An activator for hydrogenation reaction, comprising an intermetallic compound represented by formula (1):

$$RTX \quad (1)$$

wherein R represents a lanthanoid element,
T represents a transition metal in period 4 or period 5 in the periodic table, and
X represents Si, Al or Ge.

[2] A method for using an intermetallic compound represented by formula (1), comprising contacting the intermetallic compound with hydrogen to activate a bond in a hydrogen molecule:

$$RTX \quad (1)$$

wherein R represents a lanthanoid element,
T represents a transition metal in period 4 or period 5 in the periodic table, and
X represents Si, Al or Ge.

[3] A catalyst comprising an intermetallic compound represented by formula (1):

$$RTX \quad (1)$$

wherein R represents a lanthanoid element,
T represents a transition metal in period 4 or period 5 in the periodic table, and
X represents Si, Al or Ge.

[4] The catalyst according to [3], wherein the catalyst is a catalyst for ammonia synthesis.

[5] A transition metal-supported intermetallic compound comprising a transition metal M supported on an intermetallic compound represented by formula (1):

$$RTX \quad (1)$$

wherein R represents a lanthanoid element,
T represents a transition metal in period 4 or period 5 in the periodic table, and
X represents Si, Al or Ge.

[6] An activator for hydrogenation reaction, comprising the transition metal-supported intermetallic compound according to [5].

[7] A method for using the transition metal-supported intermetallic compound according to [5], comprising contacting the intermetallic compound with hydrogen to activate a bond in a hydrogen molecule.

[8] A catalyst comprising the transition metal-supported intermetallic compound according to [5].

[9] The catalyst according to [8], wherein the catalyst is a catalyst for ammonia synthesis.

[10] An intermetallic compound-hydrogen complex represented by formula (2), wherein the intermetallic compound is capable of storing and releasing hydrogen reversibly and the complex is capable of releasing hydrogen at 400° C. or less:

$$RTX \cdot aH \quad (2)$$

wherein R represents a lanthanoid element,
T represents a transition metal in period 4 or period 5 in the periodic table,
X represents Si, Al or Ge and
a represents a number of 0.5 or more and 1.5 or less.

[11] A catalyst comprising the complex according to [10].

[12] The catalyst according to [11], wherein the catalyst is a catalyst for ammonia synthesis.

[13] A transition metal-supported complex comprising a transition metal M supported on the complex according to [10].

[14] A catalyst comprising the transition metal-supported complex according to [13].

[15] The catalyst according to [14], wherein the catalyst is a catalyst for ammonia synthesis.

[16] A method for producing ammonia, comprising contacting nitrogen and hydrogen with a catalyst, wherein the catalyst is a catalyst according to [4], [9], [12] or [15].

Effect of the Invention

The intermetallic compound and the transition metal-supported intermetallic compound used in the present invention have excellent hydrogen storage/release properties and ammonia synthesis activity, and have excellent stability under temperature and pressure conditions lower than those of the Haber-Bosch process. Thus, they are useful as a catalyst for ammonia synthesis and a catalyst for various hydrogenation reactions.

DESCRIPTION OF EMBODIMENTS

<Ternary Intermetallic Compound>

Figure 1:
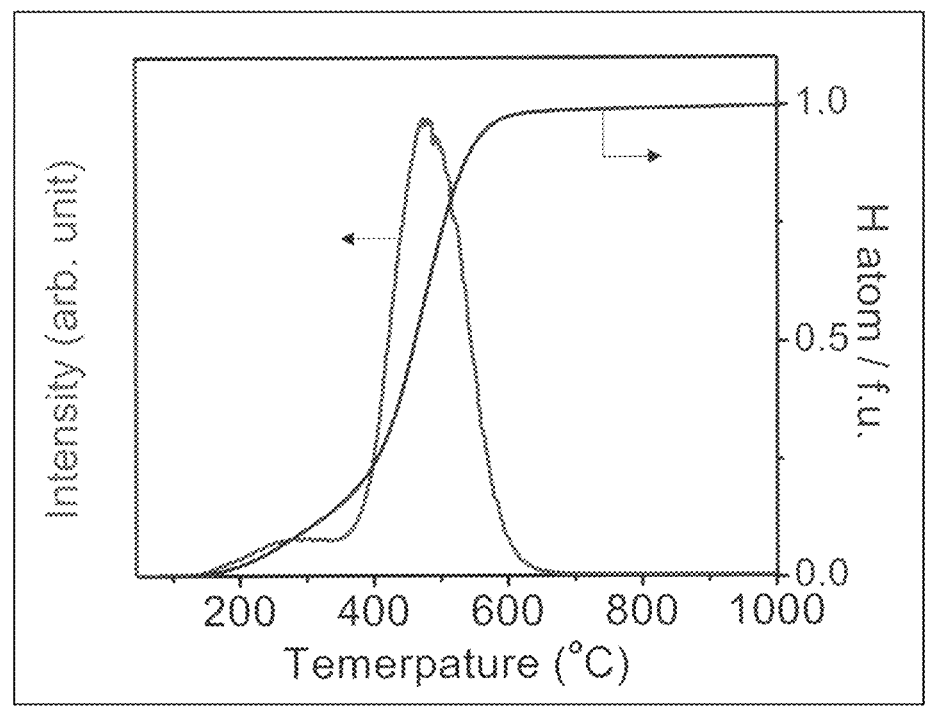
FIG. 1 shows the result of analyzing release profile of hydrogen from hydrogenated LaCoSi caused by temperature increase.

The intermetallic compound used in the present invention is an intermetallic compound represented by the following formula (1).

$$RTX \quad (1)$$

wherein R represents a lanthanoid element,
T represents a transition metal in period 4 or period 5 in the periodic table, and
X represents Si, Al or Ge.

R represents a lanthanoid element, and examples thereof include La, Ce, Pr, Nd, Sm, Gd, Tb, Dy, Ho, Er, Tm, Yb and Lu.

The lanthanoid elements have a characteristic of causing little change in their physical properties such as free electrons and work function even when the number of valence electrons (the atomic number) is increased, because electrons are placed in 4f orbital. In other words, as long as their crystal structure remains the same, properties of the above RTX are usually independent of the type of the lanthanoid elements R. In particular, La, Gd and Ce of the lanthanoid elements are preferred because their Clarke number is high and they are relatively inexpensive. La and Ce are more preferred and La is particularly preferred, because they have high catalytic activity, in particular, ammonia synthesis activity described later.

T represents a transition metal in period 4 or period 5 in the periodic table. Examples thereof include Sc, Y, Mn, Fe, Co, Ni, Ru, Rh, Pd, Ti and Cu, and Sc, Y, Fe, Ru, Co, Rh, Ni, Pd and Ti are more preferred, and Sc, Fe, Ru, Co, Rh and Ti are further preferred. Sc, Co, Ru and Fe are still more preferred, and Sc and Co are particularly preferred, because they have high catalytic activity, in particular, ammonia synthesis activity described later.

X represents Si, Al or Ge. Of them, Si and Ge are preferred, and Si is more preferred, because they have high ammonia synthesis activity.

The intermetallic compound RTX used in the present invention refers to an intermetallic compound containing the above constituent elements R, T and X. The ratio of atoms R, T and X in the above RTX is not particularly limited as long as the effects of the present invention are obtained. Usually the compound has an atomic ratio suitable for producing the effect of the present invention depending on the combination of the constituent elements.

When the above RTX is represented as RrTtXn, the ratio of the number of atoms t of T to the number of atoms r of R, t/r, is not particularly limited, and is usually 0.2 or more, preferably 0.3 or more, and more preferably 0.5 or more, and usually 3 or less, preferably 2 or less, further preferably 1.5 or less, and most preferably 1, from the viewpoint of high ammonia synthesis activity described later.

Likewise, the ratio of the number of atoms of X to the number of atoms of R, n/r, is not particularly limited, and is usually 0.2 or more, preferably 0.3 or more, and more preferably 0.5 or more, and usually 3 or less, preferably 2 or less, further preferably 1.5 or less, and most preferably 1, from the viewpoint of high ammonia synthesis activity described later.

Specific examples of intermetallic compounds represented by formula (1) include LaCoSi LaRuSi, LaFeSi, LaMnSi, LaTiSi, LaCuSi, LaCoGe, LaRuSi, CeCoSi, GdCoSi, CeFeSi, GdFeSi, LaScSi, CeScSi, GdScSi, GdTiSi, GdTiGe, LaScGe, CeScGe, GdScGe and LaCuSi. Of them, LaCoSi, LaRuSi, LaFeSi, LaScSi, CeScSi, GdScSi, GdTiSi and the like are preferred because of their high activity. When RTX is used alone, LaCoSi, LaRuSi and LaFeSi are preferred because of their high activity. When RTX is used together with a supporting metal M described later, for example, LaScSi, CeScSi, GdScSi, GdTiSi, LaCoSi, LaRuSi and LaFeSi are preferred because of high ammonia synthesis activity.

The crystal structure of the RTX is not particularly limited, and the RTX has a crystal structure such as a cubic, tetragonal, hexagonal, orthorhombic, or monoclinic structure. A tetragonal structure and a hexagonal structure are preferred from the viewpoint of easiness in obtaining a single-phase crystal and high catalytic activity described later. A tetragonal structure is more preferred from the viewpoint of high ammonia synthesis activity described later, and a hexagonal structure is more preferred from the viewpoint of high catalytic activity in hydrogenation reaction described later.

It has been found in an exafs analysis that in the intermetallic compound (RTX) of formula (1), a lanthanoid (R) donates electrons to a transition metal (T), and thus the transition metal (T) is negatively charged. This realizes lower work function of the intermetallic compound of formula (1).

The work function of the intermetallic compound (RTX) of the present invention is not particularly limited, and is usually lower than that of transition metals described later, and is preferably 2.0 eV or more and 4.0 eV or less.

The work function is the minimum energy required to extract an electron from the surface of a substance, and is usually the energy difference between the vacuum level and the Fermi level. The work function of a transition metal is not particularly limited, and a preferred work function when the transition metal is used as a catalyst as described later is usually 4.5 eV or more and 5.5 eV or less. The work function of the RTX is sufficiently smaller than that of the transition metal described later. Thus, the RTX is highly capable of supplying electrons to transition metal.

The RTX used in the present invention exhibits a remarkable chemical stability. More specifically, the RTX is stable not only in the atmosphere but also in water, and their chemical properties remain unchanged even after being exposed to water.

The intermetallic compound of formula (1) by itself has not only ammonia synthesis activity, but also hydrogen storage/release properties.

In other words, the intermetallic compound RTX used in the present invention can be used as a reagent or a reaction accelerator, which supplies electrons contained in its structure. In particular, the RTX can be used, for example, alone or together with a transition metal supported thereon, as a reaction accelerator for supplying electrons to the transition metal. More specifically, the RTX can be used as a material of a catalyst which supplies electrons. The intermetallic compound RTX used in the present invention reacts with hydrogen and thus can store it in the crystal structure in the form of hydride (H—), and can release the hydride reversibly. In other words, the RTX can also be used as an activator for hydrogenation reaction, which supplies electrons, reacts with and stores the resulting hydrogen, and releases the hydrogen reversibly. More specifically, when the RTX is contacted with hydrogen, bonds between hydrogen molecules (H—H) are activated to form a hydride. By using the RTX as such an activator for hydrogenation reaction, the RTX may be used as a catalyst described later or a reaction agent using a hydride. Such a method for using the RTX enables activation of bonds in not only hydrogen molecules but also nitrogen molecules. Furthermore, the intermetallic compound of the present invention is useful as a catalyst for various hydrogenation reactions of organic compounds, such as hydrogenation, dehydrogenation, hydrogen transfer and hydrocracking.

The method of synthesizing the intermetallic compound of formula (1) is not particularly limited, and the compound may be produced by a known method usually used. More specifically, the compound is synthesized by, for example, a solid-state reaction, arc melting and arc evaporation.

In the solid-state reaction, a lanthanoid element represented by R, a transition metal represented by T, and Si or Ge are mixed at a stoichiometric ratio, and the mixture is baked. As R, T and X, materials which can be usually used as raw materials of R, T and X, in a particulate, massive or other form, may be suitably used. The temperature of calcination is not particularly limited, and is usually 1,000° C. or more, and preferably 1,100° C. or more, and usually 1,200° C. or less.

In arc melting, a mixture of R, T and X is melted in vacuum to give RTX. Conditions of arc melting are not particularly limited, and arc melting may be performed by suitably selecting conditions usually employed within the range in which R and T are melted to form RTX.

After preparing RTX by the above method, RTX may be heated at higher temperature or, more specifically, annealed to form RTX in a desired crystal form. Conditions of annealing are not particularly limited, and known conditions may be suitably used. Conditions in which a desired crystal form can be prepared may be employed.

In arc evaporation, a base material containing R, T and X is evaporated by heating by arc discharge, and the vapor is collected to give RTX. Conditions of arc evaporation are not particularly limited, and arc evaporation may be performed by suitably selecting conditions usually employed within the range in which a desired RTX can be formed.

In the above method, the composition of base materials may be suitably adjusted so as to be matched with the desired ratio of constituent elements, depending on the difference in the vapor pressure of the elements. More specifically, when the constituent elements include an element with high vapor pressure, the composition can be adjusted by using, as a base material, an intermetallic compound in which the ratio of the element with high vapor pressure is lower than the ratio of elements in a desired RTX.

Arc evaporation may be performed in an atmosphere of various reactive gases. The composition of gas is not particularly limited. In general, arc evaporation is preferably performed in the coexistence of hydrogen and argon gas.

The temperature of heating in arc evaporation is not particularly limited. Since the resulting RTX is usually stable in the air or water, it can be easily pulverized and processed into various shapes for use. RTX may be suitably pulverized and powdered by a known method, by using, for example, an agate mortar or a ball mill.

Furthermore, in arc evaporation described above, usually RTX having an extremely small particle size, more specifically a particle size of about a few nanometers, can be obtained.

The intermetallic compound represented by RTX may be in a massive or powdery form, or may be formed into a molded article such as a porous body, a solid sintered body or thin film. The form of the molded article is not particularly limited.

In the case of a powder, the particle size of the powder is not particularly limited. The powder has a particle size of usually 10 nm or more and 10 μm or less. The smaller the particle size is, the more it is preferable, because the particle size is advantageous for the reaction when the powder is used as a catalyst.

The BET specific surface area of the intermetallic compound used in the present invention is not particularly limited. Usually, the intermetallic compound preferably has a BET specific surface area of 0.5 m$^2$/g or more and 70 m$^2$/g or less.

The intermetallic compound used in the present invention may be used after being subjected to various surface treatments. More specifically, the intermetallic compound may be used after being subjected to a surface treatment using an acid or a chelating reagent.

Figure 4:
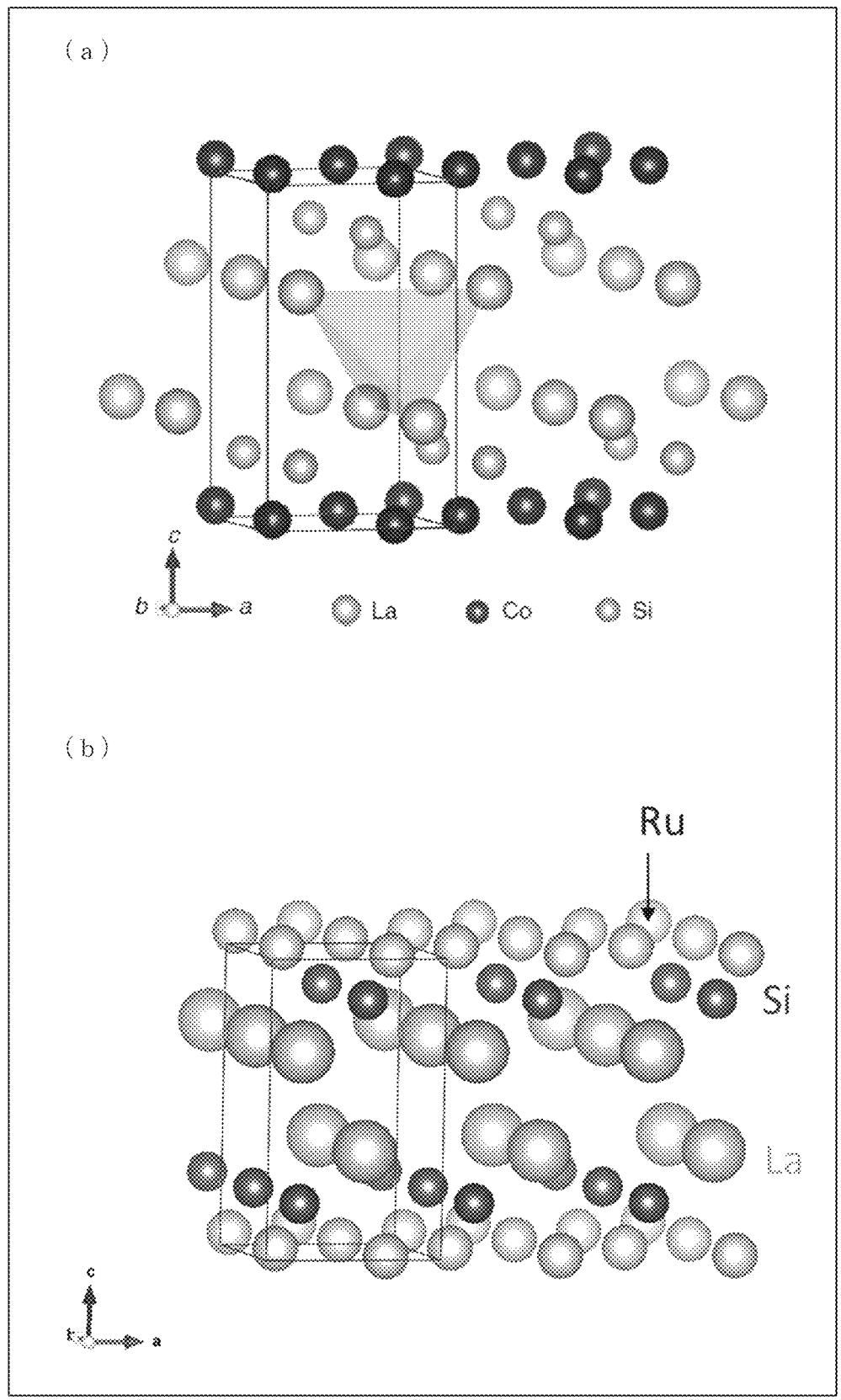
FIG. 4 shows an example of a structure of an intermetallic compound RTX used in the present invention. (a) shows the structure of LaCoSi and (b) shows the structure of LaRuSi.

As shown in FIG. 4, crystal of the intermetallic compound RTX used in the present invention usually has a structure in which the respective layers of R, T and X, which are the constituent elements thereof, (hereinafter referred to as a layer R, a layer T and a layer X) are stacked. The crystal structure is most stable when the layer R appears on the surface. Thus, most of the surface of the intermetallic compound is usually covered with the layer R when the compound is produced by a method such as arc melting and when subsequently the compound is formed into a desired shape.

It is preferable to perform surface treatment because the layer R on the surface of the intermetallic compound is removed by surface treatment, and due to an increased proportion of T appearing on the surface, electrons are supplied from lanthanoid (R), and the number of negatively charged transition metal atoms (T) (the number of active sites) is increased. Using the compound as a catalyst is preferred because the performance of the catalyst is improved.

Surface treatment reagents are not particularly limited as long as the above effect is obtained, and usually examples thereof include acids and chelating reagents. Examples of acids include, but are not limited to, inorganic acids such as hydrochloric acid, sulfuric acid, phosphoric acid, hydrofluoric acid, HF—BF3 and boric acid; organic acids such as monocarboxylic acids including formic acid, acetic acid, propionic acid, butyric acid, isobutyric acid and pentanoic acid; dicarboxylic acids including oxalic acid and succinic acid; and halogen-containing carboxylic acids including chloroacetic acid and fluoroacetic acid. Hydrochloric acid and formic acid are preferred because of easy handling.

The concentration of an acid is not particularly limited, and it is usually preferable to use a dilute acid in consideration of treating only the surface.

Examples of chelating reagents include, but are not limited to, disodium ethylenediaminetetraacetate (EDTA), citric acid, gluconic acid, nitrilotriacetic acid, diethylenetriamine pentaacetic acid, hydroxyethylenediamine triacetic acid, triethylenetriamine hexaacetic acid, 1, 3-propanediamine tetraacetic acid, 1, 3-diamino 2-hydroxypropane tetraacetic acid, hydroxyethylimino diacetic acid, dihydroxyethylglycine, glycol ether diamine tetraacetic acid, dicarboxymethyl glutamic acid, ethylenediamine disuccinic acid, hydroxyethylidene diphosphonic acid, nitrilotris, phosphonobutane tricarboxylic acid and ethylenediamine tetramethylenephosphonic acid, and EDTA is preferred.

<Transition Metal-Supported Intermetallic Compound>

In the transition metal-supported intermetallic compound of the present invention, a transition metal M is supported on an intermetallic compound represented by the above-mentioned formula (1).

<Transition Metal M>

A transition metal M is a metal supported on the intermetallic compound (1). The transition metal M may be a metal of group 4 to group 11, and is more preferably a metal of group 8, group 9 or group 10 in the periodic table. Specific examples thereof include Fe, Co, Ni, Ru, Rh, Pd, Os, Ir and Pt, more preferably Fe, Ru, Co, Rh, Ni and Pd, and further preferably Fe, Ru, Co and Rh. Fe, Ru and Co are more preferred because they are suitable as a catalyst for ammonia synthesis described later. Of them, Ru is most preferred because of the highest activity. These transition metals can be used alone or in combination of two or more transition metals.

<Supporting Transition Metal>

The method of supporting a transition metal on the intermetallic compound (1) is not particularly limited, and a known method may be used. A transition metal or a compound which is a precursor of a transition metal (hereinafter referred to as a transition metal compound) is supported thereon to prepare a transition metal-supported intermetallic compound. Usually, a method is employed, in which method a transition metal compound, which is a compound of a transition metal to be supported and can be converted into a transition metal by reduction or thermal decomposition, is supported on the intermetallic compound (1) and then converted into a transition metal. This method can be performed by, for example, mixing a transition metal compound and the intermetallic compound (1) and thermally decomposing the mixture.

The above transition metal compound is not particularly limited, and for example, an inorganic compound of a transition metal and an organic transition metal complex, which are easy to be thermally decomposed, may be used. More specifically, a complex of a transition metal, an oxide of a transition metal, a salt of a transition metal, such as nitrate and hydrochloride, and the like may be used.

Of the transition metal compounds, examples of Ru compounds include triruthenium dodecacarbonyl [$Ru_3(CO)_{12}$], dichlorotetrakis(triphenylphosphine) ruthenium (II) [$RuCl_2(PPh_3)_4$], dichlorotris(triphenylphosphine) ruthenium (II) [$RuCl_2(PPh_3)_3$], tris(acetylacetonato) ruthenium (III) [$Ru(acac)_3$], ruthenocene [$Ru(C_5H_5)$], ruthenium nitrosyl nitrate [$Ru(NO)(NO_3)_3$], potassium ruthenate, ruthenium oxide, ruthenium nitrate and ruthenium chloride.

Examples of Fe compounds include pentacarbonyl iron [$Fe(CO)_5$], dodecacarbonyl triiron [$Fe_3(CO)_{12}$], nonacarbonyl iron [$Fe_2(CO)_9$], tetracarbonyl iron iodide [$Fe(CO)_4I$], tris(acetylacetonato) iron (III) [$Fe(acac)_3$], ferrocene$_2$ [$Fe(C_5H_5)_2$], iron oxide, iron nitrate and iron chloride ($FeCl_3$).

Examples of Co compounds include cobalt octacarbonyl [$Co_2(CO)_8$], tris(acetylacetonato) cobalt (III) [$Co(acac)_3$], cobalt (II) acetylacetonate [$Co(acac)_2$], cobaltocene [$Co(C_5H_5)_2$], cobalt oxide, cobalt nitrate and cobalt chloride.

Of these transition metal compounds, carbonyl complexes of a transition metal, such as [$Ru_3(CO)_{12}$], [$Fe(CO)_5$], [$Fe_3(CO)_{12}$], [$Fe_2(CO)_9$] and [$Co_2(CO)_8$] are preferred because in the case of those carbonyl complexes, a transition metal is supported by heating after the complex is supported, and thus the reduction treatment described later can be omitted in the production of the transition metal-supported intermetallic compound of the present invention.

The amount to be used of the transition metal compound is not particularly limited, and may be adjusted so as to achieve the desired amount of support. The amount is usually 0.01% by mass or more, preferably 0.05% by mass or more, and more preferably 0.1% by mass or more, and usually 30% by mass or less, preferably 20% by mass or less, and more preferably 15% by mass or less with respect to the mass of the intermetallic compound used.

For supporting a transition metal, a method such as an impregnation method, a physical mixing method, a sputtering method or a CVD method (chemical vapor deposition) may be used for the production.

The following process may be used as an impregnation method. For example, the above intermetallic compound is added to a solution of the above transition metal compound, and the mixture is stirred. Solvents at that stage are not particularly limited, and water or various organic solvents may be used. The transition metal compound may be dissolved or dispersed in a solvent.

Next, the mixture is heated and dried in a flow of inert gas such as nitrogen, argon or helium, or in vacuum. The temperature of heating at that stage is not particularly limited, and is usually 50° C. or more and 300° C. or less. The time of heating is not particularly limited, and is usually 30 minutes or more and 20 hours or less.

In the case of a transition metal compound which will be converted into a transition metal by thermal decomposition, usually transition metal is supported on the intermetallic compound at that stage to form a transition metal-supported intermetallic compound of the present invention (hereinafter also referred to as a "metal-supported body of the present invention").

When a transition metal compound other than the transition metal compound which will be converted into transition metal by thermal decomposition is used, usually a transition metal compound dried is reduced to form a metal-supported body of the present invention.

The method of reducing the transition metal compound (hereinafter referred to as reduction treatment) is not particularly limited as long as the method does not interfere with the object of the present invention. Examples thereof include a method of carrying out reduction in an atmosphere containing a reducing gas, and a method in which a reducing reagent such as $NaBH_4$, $NH_2NH_2$ or formalin is added to a solution containing the above transition metal compound to deposit transition metal on the surface of the intermetallic compound. The method of carrying out reduction in an atmosphere containing a reducing gas is preferably used. Examples of reducing gases described above include hydrogen, ammonia, methanol (vapor), ethanol (vapor), methane and ethane.

Furthermore, in the reduction treatment, a component other than the reducing gas, which does not interfere with the object of the present invention, in particular, an ammonia synthesis reaction, may coexist in the reaction system. More specifically, in the reduction treatment, a gas other than reducing gas such as hydrogen, which does not interfere with the reaction, e.g., argon or nitrogen, may coexist, and nitrogen preferably coexists.

When the above reduction treatment is carried out in a gas containing hydrogen and nitrogen coexists with hydrogen, the reduction treatment can be carried out concurrently with production of ammonia described later. In other words, when the metal-supported body of the present invention is used as a catalyst for ammonia synthesis described later, the transition metal compound may be reduced and converted into a transition metal by placing the transition metal compound supported on the intermetallic compound under conditions of ammonia synthesis reaction.

The temperature of the reduction treatment is not particularly limited, and the reduction treatment is performed at usually 200° C. or more, and preferably 300° C. or more, and usually 1,000° C. or less, and preferably 600° C. or less. When the reduction treatment is performed within the above temperature range, the above transition metal grows sufficiently to a suitable extent.

The pressure of the reduction treatment is not particularly limited, and is usually 0.01 MPa or more and 10 MPa or less. A pressure in the reduction treatment the same as the pressure in the synthesis of ammonia described later eliminates the need of a complicated procedure, and this is advantageous in terms of production efficiency.

The time of the reduction treatment is not particularly limited, and is usually 1 hour or more, and preferably 2 hours or more when the reduction treatment is performed at normal pressure.

The time is preferably 1 hour or more when the reduction treatment is performed under a condition of a high reaction pressure of 1 MPa or more, for example.

The physical mixing method is a method in which the intermetallic compound and the transition metal compound are mixed in a solid state and then the mixture is heated in a flow of inert gas such as nitrogen, argon or helium, or in vacuum. The temperature and the time of heating are the same as those in the above impregnation method. The above reduction treatment is performed to give a metal-supported body of the present invention.

In the sputtering method, for example, voltage is applied to ions such as $Ar^+$ to accelerate them and the ions are bombarded on the surface of transition metal to evaporate the metal on the surface, thereby forming transition metal directly on the surface of the intermetallic compound.

In the CVD method, a complex of transition metal is evaporated by heating in vacuum and attached to the intermetallic compound, and the compound is continuously heated in a reducing atmosphere or in vacuum to reduce the transition metal compound to give the transition metal-supported intermetallic compound. The method of reduction is the same as the method of the above reduction treatment.

The temperature of heating is preferably 100 to 400° C.

The ratio of a transition metal M to the intermetallic compound (1) is preferably 0.1% by mass or more and 30% by mass or less in consideration of the catalytic activity and cost when the compound is used as a supported metal catalyst described later. The ratio is more preferably 0.02% by mass or more, and further preferably 0.05% by mass or more, and more preferably 20% by mass or less, and further preferably 10% by mass or less.

The transition metal-supported intermetallic compound of the present invention preferably has a BET specific surface area of about 1 to 3 m²/g. The BET specific surface area of the transition metal-supported intermetallic compound is usually similar to the BET specific surface area of the intermetallic compound.

The degree of dispersion of a transition metal such as Ru supported on the intermetallic compound is not particularly limited, and is usually 2.0% or more and 40% or less. The degree of dispersion of a transition metal (%) is a physical quantity representing homogeneity of a catalytically active metal on the surface of a substrate. The higher the degree of dispersion, the better it is. The degree of dispersion is determined based on the assumption that a CO molecule is adsorbed to a Ru atom.

The transition metal-supported intermetallic compound can be molded using a usual molding method and used as a molded article. Specific examples of shapes include a granule, a sphere, a tablet, a ring, a macaroni-like shape, a four-leaf shape, a cube and a honeycomb shape. A support may be coated with the transition metal-supported intermetallic compound and then the resultant is used.

The transition metal-supported intermetallic compound of the present invention is an electride, i.e., a compound that has a potent ability to supply electrons to transition metal supported. Since the transition metal-supported intermetallic compound is stable in the atmosphere and water, the compound is useful as various supported metal catalysts.

The transition metal-supported intermetallic compound of the present invention may be directly used as a supported metal catalyst of the present invention, or may be molded according to need. Although a component other than the intermetallic compound and the transition metal may also be contained as long as the effects of the present invention are not damaged, the metal-supported product of the present invention is preferably usually used directly.

Components other than the intermetallic compound and the transition metal, such as $SiO_2$, $Al_2O_3$, $ZrO_2$, MgO, activated carbon, graphite and SiC may also be contained as a carrier of the intermetallic compound.

The shape of the supported metal catalyst of the present invention is not particularly limited, and is the same as that of the transition metal-supported intermetallic compound. The particle size of the supported metal catalyst is not particularly limited, and the supported metal catalyst has a particle size of usually 10 nm or more and 50 μm or less.

The particle size of the transition metal in the supported metal catalyst of the present invention is not particularly limited, and the transition metal has a particle size of usually 1 nm or more and 100 nm or less. The transition metal has a particle size of preferably 10 nm or less, and more preferably 5 nm or less, with which the number of step sites, i.e., active sites for dissociation of nitrogen, is increased.

The supported metal catalyst of the present invention is useful as a catalyst for various hydrogenation reactions of organic compounds, such as hydrogenation, hydrogen transfer and hydrocracking, and in particular, as a catalyst for producing ammonia. This is because since the supported metal catalyst of the present invention contains in its structure the above transition metal-supported intermetallic compound which has properties of an electride, the supported metal catalyst has a potent ability to supply electrons (low work function). In particular, when the supported metal catalyst is used as a catalyst for ammonia synthesis, the supported metal catalyst facilitates dissociation of strong nitrogen molecules (N≡N), and thus is preferred as a catalyst for producing ammonia.

<Intermetallic Compound-Hydrogen Complex>

The intermetallic compound-hydrogen complex of the present invention is a complex with hydrogen stored in the intermetallic compound represented by formula (1), and is represented by the following formula (2).

$$RTX \cdot aH \tag{2}$$

wherein R represents a lanthanoid element,

T represents a transition metal in period 4 or period 5 in the periodic table,

X represents Si, Al or Ge and a represents a number of 0.5 or more and 1.5 or less.

The intermetallic compound (1) can store and release hydrogen reversibly. When the intermetallic compound (1) stores hydrogen and the complex (2) is formed, hydrogen in the complex (2) can be released from the complex (2) at a temperature lower than that in the case of using conventional catalysts, which is specifically usually 400° C. or less.

Here, reversible storage and release of hydrogen means that the intermetallic compound (1) can store hydrogen and the resulting complex with the intermetallic compound (1) can freely release the hydrogen stored repeatedly under a pre-determined condition.

The temperature at which hydrogen is released from the complex (2) (hereinafter referred to as release temperature) is a temperature at which release of hydrogen starts as the complex (2) is heated. More specifically, the release temperature means a temperature at which release of hydrogen starts when the temperature of the complex (2) is increased by heating according to the method of measuring hydrogen storage capacity described later.

The complex (2) is produced by contacting hydrogen with the intermetallic compound (1). The method of production is not particularly limited, and the complex may be produced by a known method of storing hydrogen in the intermetallic compound (1). Examples thereof include a method in which the intermetallic compound (1) is heated in a hydrogen gas atmosphere and a method in which the intermetallic compound (1) is pressurized in a hydrogen gas atmosphere.

The temperature in the production of the complex (2) is not particularly limited, and is usually room temperature or more, preferably 100° C. or more, and more preferably 200° C. or more, and usually 500° C. or less. Likewise, the pressure in the production is not particularly limited, and is usually 1.0 MPa or more. The time of heating is not particularly limited, and is usually 2 hours or more, and preferably 8 hours or more, and usually 12 hours or less.

The complex (2) stores hydrogen and thus is useful as a catalyst for various hydrogenation reactions of organic compounds, such as hydrogenation, hydrogen transfer and hydrocracking, and in particular, as a catalyst for producing ammonia. Furthermore, since the complex exhibits properties of releasing hydrogen after storage, the complex can also be used for dehydrogenation of organic compounds.

<Transition Metal-Supported Intermetallic Compound-Hydrogen Complex>

The transition metal-supported intermetallic compound-hydrogen complex of the present invention is a complex with hydrogen stored in a compound with a transition metal M supported on an intermetallic compound represented by formula (1). This is a complex with hydrogen stored in the transition metal-supported compound, represented by formula (2).

The complex is produced by contacting hydrogen with the transition metal-supported intermetallic compound. The same method as the method of producing the above intermetallic compound-hydrogen complex may be used. The method of production is not particularly limited, and as described above, the complex may be produced by a method similar to a known method of storing hydrogen in the intermetallic compound (1).

This complex also stores hydrogen and thus is useful as a catalyst for various hydrogenation reactions of organic compounds, such as hydrogenation, hydrogen transfer and hydrocracking, and in particular, as a catalyst for producing ammonia.

<Production of Ammonia>

The method for producing ammonia of the present invention (hereinafter may be referred to as the method of the present invention) uses the intermetallic compound, the supported metal catalyst, or the complex of the present invention as a catalyst to produce ammonia by reacting hydrogen and nitrogen on the catalyst.

Referring to a specific method of production, the method is not particularly limited as long as it is a method of synthesizing ammonia by contacting hydrogen and nitrogen with each other on the above catalyst. Ammonia may be suitably produced according to a known method of production.

In the method for producing ammonia of the present invention, usually ammonia is produced by heating a catalyst when hydrogen and nitrogen are contacted with each other on the catalyst.

The reaction temperature in the production method of the present invention is not particularly limited, and is usually 200° C. or more, preferably 250° C. or more, and more preferably 300° C. or more, and usually 600° C. or less, preferably 500° C. or less, and more preferably 450° C. or less. Because synthesis of ammonia involves an exothermic reaction, low temperature regions are more advantageous for production of ammonia based on the chemical equilibrium theory. However, it is preferable to perform the reaction in the above temperature range in order to achieve a sufficient rate of producing ammonia.

The molar ratio of nitrogen and hydrogen to be contacted with the above catalyst in the production method of the present invention is not particularly limited, and is usually 0.4 or more, preferably 0.5 or more, and more preferably 1 or more, and usually 10 or less, and preferably 5 or less in terms of the ratio of hydrogen to nitrogen ($H_2/N_2$ (volume/volume)).

The reaction pressure in the production method of the present invention is not particularly limited, and is usually a pressure of a mixed gas containing nitrogen and hydrogen of 0.01 MPa or more, and preferably 0.1 MPa or more, and usually 20 MPa or less, preferably 15 MPa or less, and more preferably 10 MPa or less. Furthermore, the reaction is preferably performed under a pressurizing condition of more than atmospheric pressure in consideration of practical use.

In the production method of the present invention, water content and oxide attached to the catalyst is preferably removed by using, for example, hydrogen gas before contacting nitrogen and hydrogen with the catalyst. Examples of methods of removal include a reduction treatment.

In the production method of the present invention, the content of water in nitrogen and hydrogen used in the production method of the present invention is preferably small in order to obtain a higher yield of ammonia. The content of water is not particularly limited, and the total content of water in a mixed gas of nitrogen and hydrogen is usually 100 ppm or less, and preferably 50 ppm or less.

In the production method of the present invention, the shape of the reaction vessel is not particularly limited, and a reaction vessel usually used for an ammonia synthesis reaction may be used. Examples of specific reaction systems to be used include a batch reaction system, a closed circulation reaction system and a flow reaction system. Of them, a flow reaction system is preferred from a practical point of view. Furthermore, any of a method using one reactor filled with a catalyst, a method in which a plurality of reactors filled with a catalyst are connected, and a method using a reactor having a plurality of reaction layers in the same reactor may be used.

The reaction of synthesizing ammonia from hydrogen and nitrogen is an exothermic reaction which involves volume contraction, and thus reaction heat is preferably removed in order to improve the yield of ammonia from an industrial point of view. A usually used, known reactor equipped with a unit for removing heat may be used. More specifically, for example, a method in which a plurality of reactors filled with a catalyst are connected in series and heat is removed with an intercooler provided at the outlet of each of the reactors may be used.

EXAMPLES

The present invention will be described in more detail with reference to Examples shown below.

(Measurement of Hydrogen Storage Capacity)

The quantity of hydrogen in samples was determined by using a thermal desorption spectrometer. Samples to be measured (1.5 to 2.5 mg) were subjected to temperature programmed heating in ultrahigh vacuum, and hydrogen molecules released from the sample by heating was detected with a quadrupole mass spectrometer.

[Conditions of Measurement]

Measuring instrument: Thermal desorption spectrometer TDS 1400TV (made by ESCO, Ltd.)

Degree of vacuum: $3.0 \times 10^{-7}$ Pa

Rate of temperature increase: 10° C./min (Measurement of Work Function: Ultraviolet Excited Photoelectron Spectroscopy (UPS))

Measuring equipment: VGS Class 150 electron analyzer

Excitation light: He I 21.2 eV

Condition of measurement: applied voltage 10 V (Atomic Ratio on Surface: XPS Measurement)

Name of equipment: ESCA-3200 made by Shimadzu Corporation

X-ray source: MgKα

Applied voltage: 8 kV

Degree of vacuum: $1 \times 10^{-6}$ Pa or less

Example 1

<Synthesis of LaCoSi>

2.8 g (0.02 mol) of lanthanum (manufactured by Kojundo Chemical Lab. Co., Ltd.: particles, purity 99.9%), 1.2 g (0.02 mol) of cobalt (manufactured by Kojundo Chemical Lab. Co., Ltd.: purity 99.04) and 0.56 g (0.02 mol) of silicon (manufactured by Kojundo Chemical Lab. Co., Ltd.: purity 99.999%) were each weighed. The above materials were arc-melted in an argon atmosphere to form a massive sample, and then the sample was heat-treated in vacuum at 1,000° C. for 5 days to give an intermetallic compound LaCoSi. The intermetallic compound was pulverized in an argon atmosphere by using an agate mortar, and molded into tablets, and then the tablets were heat-treated at 800° C. for 10 days. They were pulverized again in an argon atmosphere by using the agate mortar to prepare powdery LaCoSi.

<Quantification of Hydrogen in LaCoSi>

The powdery LaCoSi obtained above was heated under conditions of 200° C. and 1.0 MPa for 8 hours and cooled to room temperature to give a sample. The hydrogen storage capacity of the sample was measured by the above method of analysis. The results of analysis are shown in FIG. 1. Release of hydrogen was observed at about 150° C., reached the maximum at about 450° C., and was observed up to about 700° C. The total amount of hydrogen released from the powdery LaCoSi was estimated, and as a result, hydrogen was contained at an atomic ratio of 1.0 per 1 mol of LaCoSi. Hydrogenated LaCoSi may be described as LaCoSi·H. The work function of LaCoSi determined by the above method was 2.7 eV.

<Supporting Ru on LaCoSi>

0.50 g of the powdery LaCoSi obtained above and 0.060 g of $Ru_3(CO)_{12}$ (equivalent to 5% by mass of metal Ru to be supported, with respect to LaCoSi to be used) (available from Aldrich, 99%) were placed in a silica glass tube, and heated in vacuum at 70° C. for 1 hour. Subsequently the same was continuously heated at 120° C. for 1 hour to attach $Ru_3(CO)_{12}$ on the surface of the powdery LaCoSi. Finally, the material was heated at 250° C. for 2 hours to thermally decompose $Ru_3(CO)_{12}$ to give a supported product with Ru supported on LaCoSi (hereinafter Ru/LaCoSi).

<Synthesis of Ammonia Using Intermetallic Compound (without Ru)>

Ammonia was synthesized using the powdery LaCoSi as a catalyst, by contacting the catalyst with a mixed gas of nitrogen and hydrogen. A quartz glass tube was packed with 0.1 g of the LaCoSi, and a reaction was performed using a fixed bed flow reactor. The concentration of water in the raw material nitrogen gas and hydrogen gas was each below the detection limit. The flow rate of the raw material gases in the reaction was 15 mL/min for nitrogen and 45 mL/min for hydrogen (a total of 60 mL/min). In the reaction, the reaction pressure was atmospheric pressure (0.1 MPa), the reaction temperature was 400° C. and the reaction time was 30 hours. The rate of production of ammonia produced by the ammonia synthesis reaction was measured with a chromatograph over time, and as a result the rate of production of ammonia was 1.3 mol/g·hr. The results are shown in Table 1.

<Synthesis of Ammonia Using Intermetallic Compound (with Ru Supported)>

Ammonia was synthesized using the Ru/LaCoSi as a catalyst, by contacting the catalyst with a mixed gas of nitrogen and hydrogen. A quartz glass tube was packed with 0.1 g of the Ru/LaCoSi, and a reaction was performed using a fixed bed flow reactor. The concentration of water in the raw material nitrogen gas and hydrogen gas was each below the detection limit. The flow rate of the raw material gases in the reaction was 15 mL/min for nitrogen and 45 mL/min for hydrogen (a total of 60 mL/min). In the reaction, the reaction pressure was atmospheric pressure (0.1 MPa), the reaction temperature was 400° C. and the reaction time was 30 hours. The rate of production of ammonia produced by the ammonia synthesis reaction was measured with a chromatograph over time, and as a result the rate of production of ammonia was 5.1 mol/g·hr. The results are shown in Table 2.

Example 2

An intermetallic compound LaRuSi was prepared in the same manner as in Example 1 except for using 2.0 g (0.02 mol) of ruthenium (manufactured by Kojundo Chemical Lab. Co., Ltd.: purity 99.9%) instead of cobalt of the materials used in Example 1. The intermetallic compound was pulverized in the same manner as in Example 1 to prepare powdery LaRuSi. The work function of LaRuSi was 2.4 eV.

Ammonia was synthesized under the same conditions as in Example 1 except for using the powdery LaRuSi as a catalyst. The rate of production of ammonia was 1.2 mmol/g·hr. The results are shown in Table 1.

Figure 2:
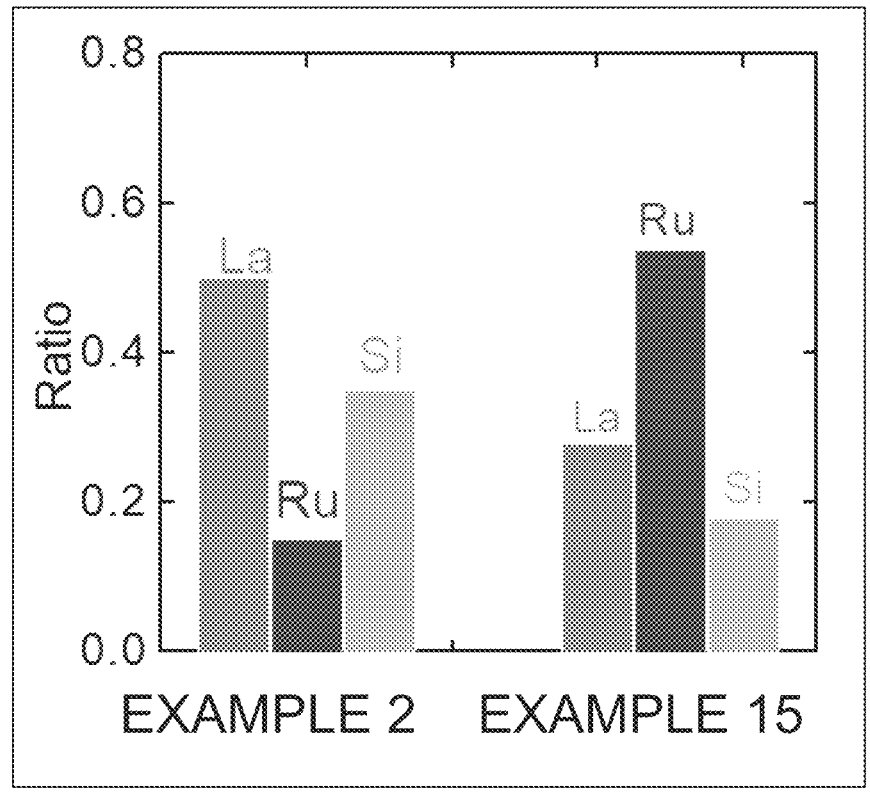
FIG. 2 shows the ratio of atoms on the surface of the intermetallic compounds of Example 2 and Example 15.

The results of analyzing the state of the surface of the powdery LaRuSi by XPS are shown in FIG. 2. The atomic ratio of the elements existing on the surface of the powdery LaRuSi was La:Ru:Si=0.5:0.15:0.35.

Example 3

An intermetallic compound LaFeSi was prepared in the same manner as in Example 1 except for using 1.1 g (0.02 mol) of iron (manufactured by Kojundo Chemical Lab. Co., Ltd.: purity 99.9%) instead of cobalt of the materials used in Example 1. The intermetallic compound was pulverized in the same manner as in Example 1 to prepare powdery LaFeSi.

Ammonia was synthesized under the same conditions as in Example 1 except for using the powdery LaFeSi as a catalyst. The rate of production of ammonia was 0.7 mmol/g·hr.

Metal Ru was supported on LaFeSi in the same manner as in Example 1 so that the proportion of Ru was 5% by mass with respect to LaFeSi to prepare a supported product Ru/LaFeSi.

Ammonia was synthesized under the same conditions as in Example 1 except for using the Ru/LaFeSi as a catalyst. The rate of production of ammonia was 5.0 mmol/g·hr. The results are shown in Table 2.

Example 4

An intermetallic compound LaCoGe was prepared in the same manner as in Example 1 except for using 1.5 g (0.02 mol) of germanium (manufactured by Kojundo Chemical Lab. Co., Ltd.: purity 99.99%) instead of silicon of the materials used in Example 1. The intermetallic compound was pulverized in the same manner as in Example 1 to prepare powdery LaCoGe.

Ammonia was synthesized under the same conditions as in Example 1 except for using the LaCoGe as a catalyst. The rate of production of ammonia was 0.5 mmol/g·hr. The results are shown in Table 1.

Example 5

An intermetallic compound GdCoSi was prepared in the same manner as in Example 1 except for using 3.1 g (0.02 mol) of gadolinium (manufactured by Kojundo Chemical Lab. Co., Ltd.: particles, purity 99.9%) instead of lanthanum of the materials used in Example 1. The intermetallic compound was pulverized in the same manner as in Example 1 to prepare powdery GdCoSi.

Ammonia was synthesized under the same conditions as in Example 1 except for using the GdCoSi as a catalyst. The rate of production of ammonia was 0.4 mmol/g·hr. The results are shown in Table 1.

Example 6

An intermetallic compound CeFeSi was prepared in the same manner as in Example 1 except for using 2.8 g (0.02 mol) of cerium (manufactured by Kojundo Chemical Lab. Co., Ltd.: particles, purity 99.9%) instead of lanthanum of the materials used in Example 3. The intermetallic compound was pulverized in the same manner as in Example 1 to prepare powdery CeFeSi.

Ammonia was synthesized under the same conditions as in Example 1 except for using the CeFeSi as a catalyst. The rate of production of ammonia was 0.3 mmol/g·hr. The results are shown in Table 1.

Example 7

An intermetallic compound LaScSi was prepared in the same manner as in Example 1 except for using 0.90 g (0.02 mol) of scandium (manufactured by Kojundo Chemical Lab. Co., Ltd.: purity 99.5%) instead of cobalt of the materials used in Example 1. The intermetallic compound was pulverized in the same manner as in Example 1 to prepare powdery LaScSi.

Metal Ru was supported on the powdery LaScSi in the same manner as in Example 1 so that the proportion of Ru was 5% by mass with respect to the powdery LaScSi to prepare a supported product Ru/LaScSi.

Ammonia was synthesized under the same conditions as in Example 1 except for using the Ru/LaScSi as a catalyst. The rate of production of ammonia was 5.4 mmol/g·hr. The results are shown in Table 2.

Example 8

An intermetallic compound CeScSi was prepared in the same manner as in Example 1 except for using 2.8 g (0.02 mol) of cerium instead of lanthanum of the materials used in Example 7. The intermetallic compound was pulverized in the same manner as in Example 1 to prepare powdery CeScSi.

Metal Ru was supported on the powdery CeScSi in the same manner as in Example 1 so that the proportion of Ru was 5% by mass with respect to the CeScSi to prepare a supported product Ru/CeScSi.

Ammonia was synthesized under the same conditions as in Example 1 except for using the Ru/CeScSi as a catalyst. The rate of production of ammonia was 5.5 mmol/g·hr. The results are shown in Table 2.

Example 9

An intermetallic compound GdScSi was prepared in the same manner as in Example 1 except for using 3.1 g (0.02 mol) of gadolinium instead of lanthanum of the materials used in Example 7. The intermetallic compound was pulverized in the same manner as in Example 1 to prepare powdery GdScSi.

Metal Ru was supported on GdScSi in the same manner as in Example 1 so that the proportion of Ru was 5% by mass with respect to GdScSi to prepare a supported product Ru/GdScSi.

Ammonia was synthesized under the same conditions as in Example 1 except for using the Ru/GdScSi as a catalyst. The rate of production of ammonia was 3.7 mmol/g·hr. The results are shown in Table 2.

Example 10

An intermetallic compound GdTiSi was prepared in the same manner as in Example 1 except for using 0.96 g (0.02 mol) of titanium (manufactured by Kojundo Chemical Lab. Co., Ltd.: purity 99.0%) instead of scandium of the materials used in Example 9. The intermetallic compound was pulverized in the same manner as in Example 1 to prepare powdery GdTiSi.

Metal Ru was supported on GdTiSi in the same manner as in Example 1 so that the proportion of Ru was 5% by mass with respect to GdScSi to prepare a supported product Ru/GdTiSi.

Ammonia was synthesized under the same conditions as in Example 1 except for using the Ru/GdTiSi as a catalyst. The rate of production of ammonia was 2.9 mmol/g·hr. The results are shown in Table 2.

Comparative Example 1

1.6 g (18.2 mmol) of yttrium and 0.31 g (10.9 mmol) of silicon were each weighed. They were arc-melted in an argon atmosphere to give an intermetallic compound $Y_5Si_3$. The resulting massive $Y_5Si_3$ was pulverized in the same manner as in Example 1 to prepare powdery $Y_5Si_3$.

Metal Ru was supported on $Y_5Si_3$ in the same manner as in Example 1 so that the proportion of Ru was 5% by mass with respect to $Y_5Si_3$ to prepare a supported product $Ru/Y_5Si_3$.

Ammonia was synthesized under the same conditions as in Example 1 except for using the $Ru/Y_5Si_3$ as a catalyst. The rate of production of ammonia was 2.1 mmol/g·hr. The results are shown in Table 2.

Comparative Example 2

An intermetallic compound $Y_5Ge_3$ was prepared in the same manner as in Comparative Example 1 except for using 0.88 g (10.0 mmol) of yttrium and 0.44 g of germanium. The resulting massive $Y_5Ge_3$ was pulverized in the same manner as in Example 1 to prepare powdery $Y_5Ge_3$.

Metal Ru was supported on $Y_5Ge_3$ in the same manner as in Example 1 so that the proportion of Ru was 5% by mass with respect to $Y_5Ge_3$ to prepare a supported product $Ru/Y_5Ge_3$.

Ammonia was synthesized under the same conditions as in Example 1 except for using the $Ru/Y_5Ge_3$ as a catalyst. The rate of production of ammonia was 1.9 mmol/g·hr. The results are shown in Table 2.

Comparative Example 3

An intermetallic compound $La_5Si_3$ was prepared in the same manner as in Comparative Example 1 except for using 2.5 g (18.2 mmol) of lanthanum and 0.31 g (10.9 mmol) of silicon. The resulting massive $La_5Si_3$ was pulverized in the same manner as in Example 1 to prepare powdery $La_5Si_3$.

Metal Ru was supported on $La_5Si_3$ in the same manner as in Example 1 so that the proportion of Ru was 5% by mass with respect to $La_5Si_3$ to prepare a supported product $Ru/La_5Si_3$.

Ammonia was synthesized under the same conditions as in Example 1 except for using the Ru/La$_5$Si$_3$ as a catalyst. The rate of production of ammonia was 4.8 mmol/g·hr. The results are shown in Table 2. Ru/La$_5$Si$_3$ was decomposed and converted into a hydride such as LaH3 during the ammonia synthesis reaction, and thus the structure of the original intermetallic compound was not maintained.

TABLE 1

|  | Material | Catalytic activity (mmol/g · hr) |
|---|---|---|
| Example 1 | LaCoSi | 1.3 |
| Example 2 | LaRuSi | 1.2 |
| Example 3 | LaFeSi | 0.7 |
| Example 4 | LaCoGe | 0.5 |
| Example 5 | GdCoSi | 0.4 |
| Example 6 | CeFeSi | 0.3 |

TABLE 2

|  | Material | Catalytic activity (mmol/g · hr) | Remarks |
|---|---|---|---|
| Example 1 | Ru/LaCoSi | 5.1 |  |
| Example 3 | Ru/LaFeSi | 5.0 |  |
| Example 7 | Ru/LaScSi | 5.4 |  |
| Example 8 | Ru/CeScSi | 5.5 |  |
| Example 9 | Ru/GdScSi | 3.7 |  |
| Example 10 | Ru/GdTiSi | 2.9 |  |
| Comparative Example 1 | Ru/Y$_5$Si$_3$ | 2.1 |  |
| Comparative Example 2 | Ru/Y$_5$Ge$_3$ | 1.9 |  |
| Comparative Example 3 | Ru/La$_5$Si$_3$ | 4.8 | Unstable |

Example 11

0.2 g of the powdery LaRuSi prepared in Example 2 was dispersed in 10 mL of 0.02 M hydrochloric acid and immersed therein with ultrasonically stirring at room temperature for 30 minutes. Subsequently, the resultant was washed with water and then dried in vacuum at room temperature to give LaRuSi which was surface-treated with hydrochloric acid (hereinafter referred to as hydrochloric acid-treated LaRuSi).

Ammonia was synthesized under the same conditions as in Example 1 except for using the hydrochloric acid-treated LaRuSi as a catalyst. The rate of production of ammonia was 1.5 mmol/g·hr. The results are shown in Table 3.

Example 12

Surface treatment was performed in the same manner as in Example 11 except for using a 10% by mass aqueous formic acid solution instead of the 0.02 M aqueous hydrochloric acid solution in Example 11 to give LaRuSi which was surface-treated with formic acid (hereinafter referred to as 10% formic acid-treated LaRuSi).

Ammonia was synthesized under the same conditions as in Example 1 except for using the 10% formic acid-treated LaRuSi as a catalyst. The rate of production of ammonia was 1.6 mmol/g·hr. The results are shown in Table 3.

Example 13

Surface treatment was performed in the same manner as in Example 11 except for using a 50% by mass aqueous formic acid solution instead of the 0.02 M aqueous hydrochloric acid solution in Example 11 to give LaRuSi which was surface-treated with formic acid (hereinafter referred to as 50% formic acid-treated LaRuSi).

Ammonia was synthesized under the same conditions as in Example 1 except for using the 50% formic acid-treated-LaRuSi as a catalyst. The rate of production of ammonia was 1.9 mmol/g·hr. The results are shown in Table 3.

Example 14

Surface treatment was performed in the same manner as in Example 11 except for using a 50% by mass aqueous acetic acid solution instead of the 0.02 M aqueous hydrochloric acid solution in Example 11 to give LaRuSi which was surface-treated with acetic acid (hereinafter referred to as acetic acid-treated LaRuSi).

Ammonia was synthesized under the same conditions as in Example 1 except for using the acetic acid-treated LaRuSi as a catalyst. The rate of production of ammonia was 1.3 mmol/g·hr. The results are shown in Table 3.

Example 15

0.2 g of the powdery LaRuSi prepared in Example 2 was immersed in 10 mL of an aqueous solution of 1 mM disodium ethylenediaminetetraacetate (hereinafter EDTA) and the mixture was stirred for 3 hours. Subsequently, the resultant was washed with water and then dried in vacuum at room temperature to give LaRuSi which was surface-treated with EDTA (hereinafter referred to as EDTA-treated LaRuSi).

Ammonia was synthesized under the same conditions as in Example 1 except for using the EDTA-treated LaRuSi as a catalyst. The rate of production of ammonia was 3.3 mmol/g·hr. The results are shown in Table 3.

Furthermore, the ratio of the elements existing on the surface of LaRuSi after the treatment with EDTA was measured by the above method, and as a result, the ratio was La:Ru:Si=0.28:0.54:0.18.

The results of analyzing the state of the surface of LaRuSi by XPS before and after the treatment with EDTA are shown in FIG. 2.

A comparison of the ratio of the elements existing on the surface before and after the treatment with EDTA shows that the EDTA treatment removes the La layer on the surface and increases the ratio of Ru exposed on the surface.

TABLE 3

|  | Surface treatment reagent | Catalytic activity (mmol/g · hr) |
|---|---|---|
| Example 2 | None | 1.2 |
| Example 11 | 0.02M hydrochloric acid | 1.5 |
| Example 12 | 10% by mass formic acid | 1.6 |
| Example 13 | 50% by mass formic acid | 1.9 |
| Example 14 | 50% by mass acetic acid | 1.3 |
| Example 15 | 1 mM EDTA | 3.3 |

Example 16

Surface treatment was performed in the same manner as in Example 15 except for using an EDTA aqueous solution having a concentration of 5 mM, instead of the 1 mM EDTA aqueous solution in Example 15.

Ammonia was synthesized under the same conditions as in Example 15 using the above as a catalyst, and as a result the rate of production of ammonia was 5.0 mmol/g·hr.

Furthermore, surface treatment was performed using an aqueous solution having an EDTA concentration of 10 mM, 50 mM, or 100 mM, separately, and ammonia was synthesized using each of them. As a result, the rate of production of ammonia was 4.3 mmol/g·hr, 2.1 mmol/g·hr and 1.7 mmol/g·hr, respectively. The results are shown in Table 4.

TABLE 4

| EDTA concentration | Catalytic activity (mmol/g · hr) |
|---|---|
| Not treated | 1.2 |
| 1 mM | 3.3 |
| 5 mM | 5.0 |
| 10 mM | 4.3 |
| 50 mM | 2.1 |
| 100 mM | 1.7 |

Example 17

The surface treatment performed in Example 16 using an aqueous solution of 5 mM EDTA was performed while changing the time of immersion in the EDTA aqueous solution. Ammonia was synthesized using, as a catalyst, the resultant obtained with each treatment time. The results are shown in Table 5.

TABLE 5

| Time of treatment with EDTA | Catalytic activity (mmol/g · hr) |
|---|---|
| Not treated | 1.2 |
| 0.5 hour | 3.6 |
| 1 hour | 3.4 |
| 3 hours | 5.0 |
| 5 hours | 5.2 |
| 11 hours | 5.4 |
| 23 hours | 5.1 |

Example 18

An intermetallic compound LaCuSi was prepared in the same manner as in Example 1 except for using copper (manufactured by Kojundo Chemical Lab. Co., Ltd., 2.25 g) instead of cobalt used as a raw material in Example 1 and using 7.3 g of lanthanum (manufactured by Kojundo Chemical Lab. Co., Ltd.) and 2.0 g of silicon (manufactured by Kojundo Chemical Lab. Co., Ltd.). The intermetallic compound was pulverized in the same manner as in Example 1 to prepare powdery LaCuSi. The composition ratio of the elements of the resulting intermetallic compound LaCuSi was La:Cu:Si=1:0.67:1.33. The resulting powder had a specific surface area of 0.9 m$^2$/g.

The work function of LaCuSi measured by the above method was 3.5 eV.

Hydrogenation reaction of nitrobenzene was performed using the resulting powdery LaCuSi as a catalyst.

Figure 3:
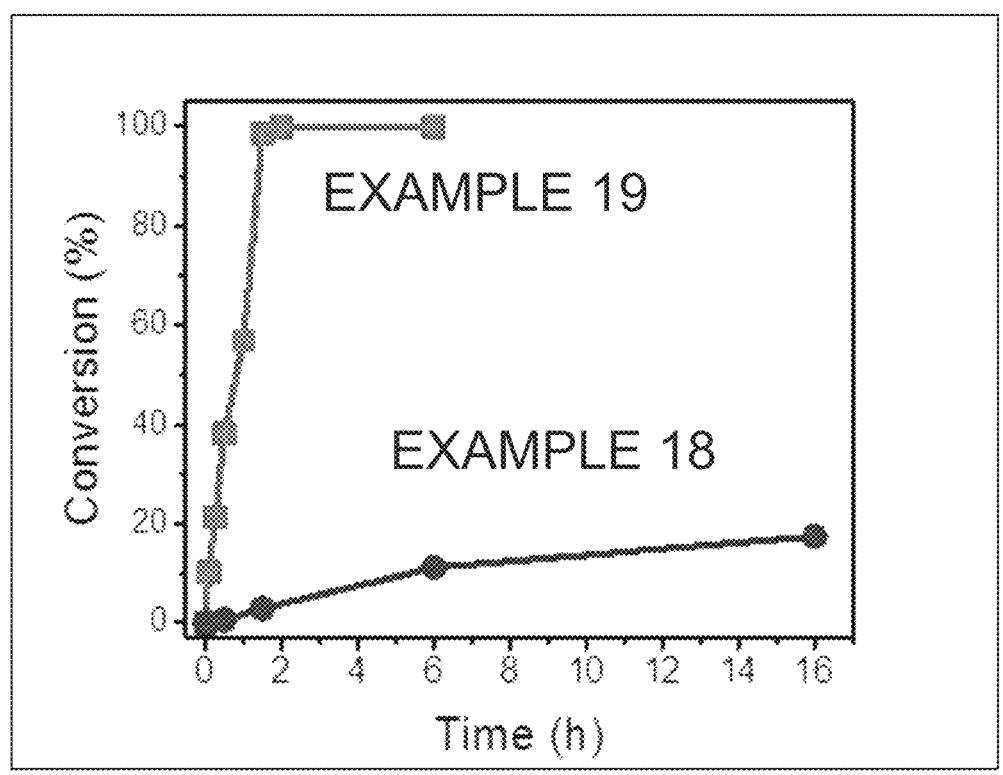
FIG. 3 shows changes in conversion in the hydrogenation reaction in Example 18 and Example 19.

61.5 mg (0.5 mmol) of nitrobenzene was dissolved in 5 mL of methanol, and 10 mg of the powdery LaCuSi was added thereto as a catalyst to perform reaction at a reaction pressure of hydrogen of 3 MPa and a reaction temperature of 120° C. As a result, they reacted quantitatively. The reaction rate was 1.0 mmol/g·hr. The results are shown in FIG. 3.

Example 19

An intermetallic compound having an atomic ratio La:Cu:Si: =1:0.065:1 (La$_1$Cu$_{0.065}$Si$_1$) was prepared in the same manner as in Example 1 except for using 10.0 g of lanthanum (manufactured by Kojundo Chemical Lab. Co., Ltd.), 0.32 g of copper (manufactured by Kojundo Chemical Lab. Co., Ltd.) and 2.1 g of silicon (manufactured by Kojundo Chemical Lab. Co., Ltd.) instead of the raw materials used in Example 1. The compound was evaporated as a base material using a mixed gas arc with a partial pressure of Ar of 0.03 MPa and a partial pressure of hydrogen of 0.03 MPa. The vapor was cooled and collected according to Ar/H$_2$ arc evaporation to synthesize nanoparticles of LaCuSi. The composition ratio of the elements of the resulting intermetallic compound LaCuSi was La:Cu:Si=1:0.67:1.33. The resulting nanoparticles of LaCuSi had a specific surface area of 65 m$^2$/g.

Hydrogenation reaction of nitrobenzene was performed in the same manner as in Example 18 using the resulting nanoparticles of LaCuSi as a catalyst. The reaction rate was 65.0 mmol/g·hr. The results are shown in FIG. 3. Both the reaction yield and the reaction rate were greatly improved compared with those in Example 18.

Example 20

Using each of LaCuSi obtained in Example 18 and Example 19 as a catalyst, nitrobenzene having a functional group was selectively hydrogenated to synthesize a corresponding aniline compound. 0.5 mmol of each nitrobenzene compound used as a raw material was dissolved in 5 mL of methanol, and 10 mg of LaCuSi was added thereto as a catalyst to perform reaction at a reaction pressure of hydrogen of 3 MPa and a reaction temperature of 120° C. For all nitrobenzene compounds, a selective hydrogenation reaction proceeded, and the intended products were obtained. The results are shown in Table 6.

Forming nanoparticles resulted in a great improvement in catalytic activity even in a selective hydrogenation reaction of nitrobenzene having various functional groups.

TABLE 6

| | Powdery LaCuSi (Example 18) | LaCuSi nanoparticles (Example 19) |
|---|---|---|
| F$_3$C-C$_6$H$_4$-NO$_2$ | 99%, 54 h | 99%, 3 h |
| CH$_3$O-C$_6$H$_4$-NO$_2$ | 99%, 24 h | 99%, 2 h |
| Cl-C$_6$H$_4$-NO$_2$ | 99%, 72 h | 99%, 24 h |
| Naphthyl-NO$_2$ | 96%, 96 h | 99%, 5 h |

TABLE 6-continued

| | Powdery LaCuSi (Example 18) | LaCuSi nanoparticles (Example 19) |
|---|---|---|
| 4-nitrobenzonitrile | 96%, 60 h | 98%, 3 h |
| 4-nitrobenzamide | 87%, 60 h | 92%, 3 h |
| methyl 4-nitrobenzoate | 99%, 192 h | 98%, 3 h |
| 4-nitroacetophenone | 93%, 48 h | 94%, 3 h |
| 4-nitrostyrene | 95%, 48 h | 97%, 1 h |

The invention claimed is:

1. A transition metal-supported intermetallic compound comprising a transition metal M supported on an intermetallic compound represented by formula (1):

$$RTX \qquad (1)$$

wherein
R represents a lanthanoid element,
T represents a transition metal in period 4 or period 5 in the periodic table, and
X represents Si, Al or Ge.

2. An activator for hydrogenation reaction, comprising the transition metal-supported intermetallic compound according to claim 1.

3. A method for using the transition metal-supported intermetallic compound according to claim 1, comprising contacting the intermetallic compound with hydrogen to activate a bond in a hydrogen molecule.

4. A catalyst comprising the transition metal-supported intermetallic compound according to claim 1.

5. The catalyst according to claim 4, wherein the catalyst is a catalyst for ammonia synthesis.

6. A transition metal-supported complex comprising a transition metal M supported on an intermetallic compound-hydrogen complex represented by formula (2), wherein the intermetallic compound is capable of storing and releasing hydrogen reversibly and the complex is capable of releasing hydrogen at 400° C. or less:

$$RTX \cdot aH \qquad (2)$$

wherein
R represents a lanthanoid element,
T represents a transition metal in period 4 or period 5 in the periodic table,
X represents Si, Al or Ge and
a represents a number of 0.5 or more and 1.5 or less.

7. A catalyst comprising the transition metal-supported complex according to claim 6.

8. The catalyst according to claim 7, wherein the catalyst is a catalyst for ammonia synthesis.

9. A method for producing ammonia, comprising contacting nitrogen and hydrogen with a catalyst, wherein the catalyst comprises an intermetallic compound represented by formula (1):

$$RTX \qquad (1)$$

wherein
R represents a lanthanoid element,
T represents a transition metal in period 4 or period 5 in the periodic table, and
X represents Si, Al or Ge.

* * * * *